(12) United States Patent
Hayashitani et al.

(10) Patent No.: US 11,574,730 B2
(45) Date of Patent: Feb. 7, 2023

(54) DATA MANAGEMENT SYSTEM, DATA MANAGEMENT METHOD, AND RECORDING MEDIUM FOR DATA MANAGEMENT PROGRAM

(71) Applicant: NEC CORPORATION, Tokyo (JP)

(72) Inventors: Masahiro Hayashitani, Tokyo (JP); Kosuke Homma, Tokyo (JP); Masahiro Kubo, Tokyo (JP); Shigemi Kitahara, Tokyo (JP)

(73) Assignee: NEC CORPORATION, Tokyo (JP)

( * ) Notice: Subject to any disclaimer, the term of this patent is extended or adjusted under 35 U.S.C. 154(b) by 377 days.

(21) Appl. No.: 16/643,319

(22) PCT Filed: Aug. 22, 2018

(86) PCT No.: PCT/JP2018/030972
§ 371 (c)(1),
(2) Date: Feb. 28, 2020

(87) PCT Pub. No.: WO2019/044621
PCT Pub. Date: Mar. 7, 2019

(65) Prior Publication Data
US 2021/0074413 A1  Mar. 11, 2021

(30) Foreign Application Priority Data
Aug. 30, 2017  (JP) .............................. JP2017-165606

(51) Int. Cl.
*G06F 17/00* (2019.01)
*G16H 40/20* (2018.01)
(Continued)

(52) U.S. Cl.
CPC ............. *G16H 40/20* (2018.01); *G06F 16/23* (2019.01); *G06F 16/242* (2019.01); *G06Q 10/02* (2013.01)

(58) Field of Classification Search
CPC ....... G16H 40/20; G06F 16/23; G06F 16/242; G06Q 10/02
See application file for complete search history.

(56) References Cited

U.S. PATENT DOCUMENTS

2007/0203761 A1* 8/2007 Keen ...................... G16H 20/40
705/5
2017/0147764 A1  5/2017 P R et al.

FOREIGN PATENT DOCUMENTS

JP  2002-215792 A  8/2002
JP  2005-182241 A  7/2005
(Continued)

OTHER PUBLICATIONS

International Search Report of PCT/JP2018/030972 dated Oct. 30, 2018 [PCT/ISA/210].
(Continued)

*Primary Examiner* — Jamara A Franklin
(74) *Attorney, Agent, or Firm* — Sughrue Mion, PLLC

(57) ABSTRACT

A data management system is provided with: a storage unit for storing examination information including at least an examination item, an examination location, a consultation location, and a required examination time, the examination item including examination names of a plurality of examinations; an acquisition unit for acquiring patient information relating to severity and an identifier for identifying the patient to be examined; a calculation unit for calculating, in accordance with the patient, the necessary travel time for traveling from the examination location or consultation location at which a completed examination or consultation was performed to the next examination location or consultation location at which the next examination or consultation subsequent to the examination or consultation is to be performed, based on the patient information and the examination information; and a generating unit for generating a
(Continued)

patient examination schedule based on the examination information, the patient information, and the travel time.

19 Claims, 9 Drawing Sheets

(51) Int. Cl.
    *G06F 16/242*      (2019.01)
    *G06F 16/23*      (2019.01)
    *G06Q 10/02*      (2012.01)

(56) References Cited

FOREIGN PATENT DOCUMENTS

| JP | 2011-090484 A | 5/2011 |
| JP | 2014-035646 A | 2/2014 |
| JP | 2016-126694 A | 7/2016 |
| JP | 2017-097878 A | 6/2017 |

OTHER PUBLICATIONS

Written Opinion of PCT/JP2018/030972 dated Oct. 30, 2018 [PCT/ISA/237].
Japanese Office Communication for JP Application No. 2019-539409 dated Dec. 15, 2021 with English Translation.

\* cited by examiner

| ITEM | EXAMINATION ROOM CONSULTATION ROOM | REQUIRED TIME | ... |
|---|---|---|---|
| EXAM A | 101 | 10 MINUTES | |
| EXAM B | 102 | 15 MINUTES | |
| EXAM C | 103 | 20 MINUTES | |
| ⋮ | ⋮ | ⋮ | ... |
| CONSULTATION A | 201 | 10 MINUTES | |
| ⋮ | ⋮ | ⋮ | |

300

| IDENTIFIER | | AGE | SEX | STATE OF PATIENT | ITEM | ⋮ |
|---|---|---|---|---|---|---|
| PATIENT ID | PATIENT NAME | | | | | |
| 0001 | AAAA | 24 | MALE | 4 | EXAM A, EXAM C | |
| 0002 | BBBB | 58 | FEMALE | 2 | EXAM A, EXAM B | |
| 0003 | CCCC | 33 | FEMALE | 3 | EXAM A, EXAM B, EXAM C | |
| 0004 | DDDD | 66 | MALE | 2 | EXAM B, EXAM C | |
| 0005 | EEEE | 47 | FEMALE | 3 | EXAM B, EXAM C | |
| 0006 | FFFF | 70 | MALE | 2 | EXAM A, EXAM B, EXAM C | |
| ⋮ | ⋮ | ⋮ | ⋮ | ⋮ | ⋮ | |

| STATE OF PATIENT | TRAVEL SPEED |
|---|---|
| 0 | $V_0$ |
| 1 | $V_1$ |
| 2 | $V_2$ |
| 3 | $V_3$ |
| 4 | $V_4$ |
| 5 | $V_5$ |

| STATE OF PATIENT | TRAVEL INTERVAL | TRAVEL TIME |
|---|---|---|
| 0 | EXAM A - EXAM B | T1 |
| 0 | EXAM A - EXAM C | T2 |
| 0 | EXAM B - EXAM C | T3 |
| 1 | EXAM A - EXAM B | T4 |
| 1 | EXAM A - EXAM C | T5 |
| 1 | EXAM B - EXAM C | T6 |
| 2 | EXAM A - EXAM B | T7 |
| 2 | EXAM A - EXAM C | T8 |
| 2 | EXAM B - EXAM C | T9 |
| 3 | EXAM A - EXAM B | T10 |
| 3 | EXAM A - EXAM C | T11 |
| 3 | EXAM B - EXAM C | T12 |
| 4 | EXAM A - EXAM B | T13 |
| 4 | EXAM A - EXAM C | T14 |
| 4 | EXAM B - EXAM C | T15 |
| 5 | EXAM A - EXAM B | T16 |
| 5 | EXAM A - EXAM C | T17 |
| 5 | EXAM B - EXAM C | T18 |

FIG. 5

DATA MANAGEMENT SYSTEM, DATA MANAGEMENT METHOD, AND RECORDING MEDIUM FOR DATA MANAGEMENT PROGRAM

CROSS REFERENCE TO RELATED APPLICATIONS

This application is a National Stage of International Application No. PCT/JP2018/030972, filed Aug. 22, 2018, claiming priority to Japanese Patent Application No. 2017-165606, filed Aug. 30, 2017, the contents of all of which are incorporated herein by reference in their entirety.

TECHNICAL FIELD

The present invention relates to a data management system, a data management method, and a recording medium for a data management program.

BACKGROUND ART

In a medical institution, a plurality of examinations are performed for a lot of patients. Therefore, examination schedules for respective patients may be preliminarily prepared so that waiting times for the examinations do not occur.

Patent Literature 1 discloses a medical care workflow system for generating an optimum examination workflow by tracking a varying examination time. Specifically, in Patent Literature 1, when a difference between estimated termination time instants in respective examination devices performing the same examination exceeds a predetermined threshold, the patients are rearranged between exchangeable examination devices so that the estimated termination time instants for the respective examination devices become even.

CITATION LIST

Patent Literature(s)
PL 1: JP 2014-035646 A

SUMMARY OF INVENTION

Technical Problem

However, Patent Literature 1 does not disclose to generate an examination schedule including a time required for traveling to an examination location when the patient undergoes a plurality of examinations. In this case, in Patent Literature 1, there is a possibility that waiting times may occur in order for the patient to undergo the examinations, and a hospital cannot perform the examinations for a lot of patients.

It is an object of the present invention to provide a data management system, a data management method, and a recording medium for a data management program which are capable of resolving the above-mentioned problem.

Solution to Problem

A data management system according to a first aspect of the present invention comprises a storage unit configured to store examination information including at least examination items which include examination names of a plurality of examinations, examination locations at which the examinations are performed, consultation locations at which consultations are performed, and required examination times which are required for the respective examinations; an acquisition unit configured to acquire patient information relating to an identifier for identifying a patient to be examined and degree of severity thereof; a calculation unit configured to calculate, in accordance with the patient, a travel time required for traveling from an examination or consultation location at which an examination or consultation already completed has been performed to a next examination or consultation location at which a next examination or consultation subsequent to the examination or consultation is to be performed, based on the patient information and the examination information; and a generating unit configured to generate an examination schedule for the patient based on the examination information, the patient information, and the travel time.

A data management system according to a second aspect of the present invention is performed by an information processing apparatus and comprises storing examination information including at least examination items which include examination names of a plurality of examinations, examination locations at which the examinations are performed, consultation locations at which consultations are performed, and required examination times which are required for the respective examinations; acquiring patient information relating to an identifier for identifying a patient to be examined and degree of severity thereof; calculating, in accordance with the patient, a travel time required for traveling from an examination or consultation location at which an examination or consultation already completed has been performed to a next examination or consultation location at which a next examination or consultation subsequent to the examination or consultation is to be performed, based on the patient information and the examination information; and generating an examination schedule for the patient based on the examination information, the patient information, and the travel time.

A recording medium according to a third aspect of the present invention records a data management program which causes a computer to execute the procedures of storing examination information including at least examination items which include examination names of a plurality of examinations, examination locations at which the examinations are performed, consultation locations at which consultations are performed, and required examination times which are required for the respective examinations; acquiring patient information relating to an identifier for identifying a patient to be examined and degree of severity thereof; calculating, in accordance with the patient, a travel time required for traveling from an examination or consultation location at which an examination or consultation already completed has been performed to a next examination or consultation location at which a next examination or consultation subsequent to the examination or consultation is to be performed, based on the patient information and the examination information; and generating an examination schedule for the patient based on the examination information, the patient information, and the travel time.

Advantageous Effect of Invention

According to the present invention, it is possible to provide a data management system, a data management method, and a recording medium for a data management program, which generate an examination schedule capable of effectively utilizing examination resources by taking a travel time between examinations into account in accordance with a state of a patient.

BRIEF DESCRIPTION OF THE DRAWINGS

FIG. 3 is a view for illustrating one example of patient information;

FIG. 4 is a view for illustrating one example of speed information representing correspondences between states of patients and travel speeds;

FIG. 5 is a view for illustrating one example of correspondence information representing correspondences between paralysis states of the patients and the travel speeds;

DESCRIPTION OF EMBODIMENTS

Now, example embodiments of the present invention will be described in detail with reference to the drawings. In the respective drawings, the same or corresponding parts are labelled with the same reference symbols and description thereof will be omitted as appropriate.

First Example Embodiment

Figures 1, 2:
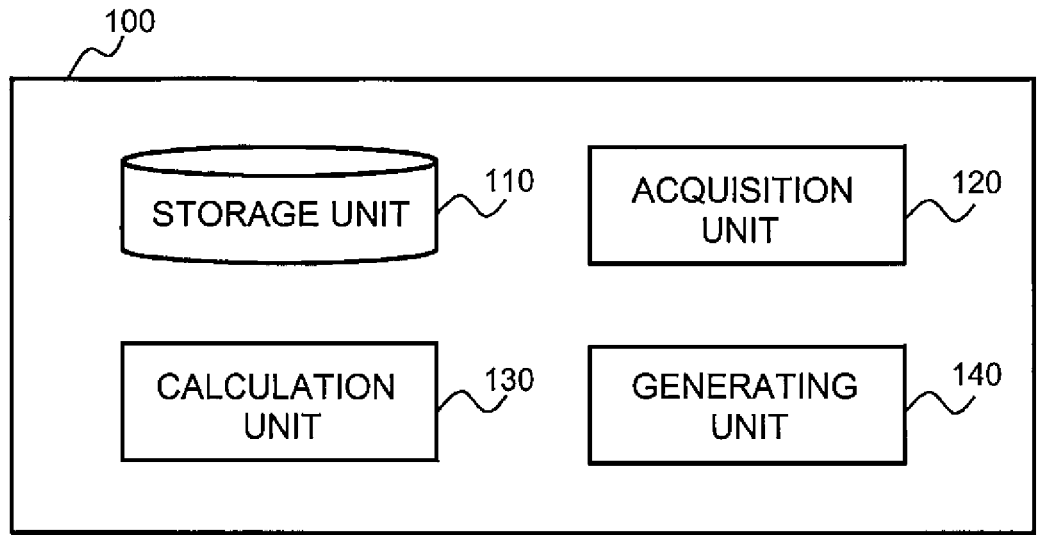
FIG. 1 is a block diagram for illustrating a configuration of a data management system according to a first example embodiment of the present invention.
FIG. 2 is a view for illustrating one example of examination information.

FIG. 1 is a block diagram for illustrating a configuration of a data management system 100 according to a first example embodiment of the present invention.

As shown in FIG. 1, the data management system 100 comprises a storage unit 110, an acquisition unit 120, a calculation unit 130, and a generating unit 140.

The storage unit 110 stores examination information including at least examination items which include examination names of a plurality of examinations, examination locations at which the examinations are performed, consultation locations at which consultations are performed, and required examination times required for the respective examinations. FIG. 2 is an example of the examination information 200 held in the storage unit 110. As shown in FIG. 2, the examination information 200 includes items of the examinations or consultations, locations of examination rooms or consultation rooms, and times required for the examinations or the consultations. For instance, as one example of the examination information 200, it is shown that an examination having an examination name of an "examination A" is performed at an "examination room 101" and has a required time of "10 minutes" required for the examination. Herein, the required examination time may be an average time required for the examination or may be a time which is set for every patient to be subjected to the examination. Furthermore, the required examination time may be a time which is set according to a state of the patient.

The acquisition unit 120 acquires, from the outside of the data management system 100, patient information 300 which includes an identifier for identifying the patient to be examined and the state of the patient such as degree of severity of a medical condition of the patient. Herein, the identifier for identifying the patient comprises, for example, a patient name and a patient ID (identification) which is a number assigned to the patient individually. The state of the patient is, for example, a paralysis state, a motor function, an age, a level of consciousness, and a cognitive level of the patient. The state of the patient acquired by the acquisition unit 120 may be one or more among the paralysis state, the motor function, the age, the level of consciousness, and the cognitive level of the patient. Furthermore, the state of the patient acquired by the acquisition unit 120 is not limited to the paralysis state, the motor function, the age, the level of consciousness, and the cognitive level of the patient. Specifically, the state of the patient acquired by the acquisition unit 120 may include information which influences a travel time required for the patient to travel from an examination location or a consultation location to a next examination location or a next consultation location.

As the paralysis state and the motor function, for example, a value which can be judged by MMT (Manual Muscle Test), FIM (Functional Independence Measure), and BI (Barthel Index) may be used. In addition, in this example embodiment, a method of judging the motor function of patient is not limited to the MMT, the FIM, and the BI and the paralysis state and the motor function of the patient may be judged by means of other methods.

As the level of consciousness and the cognitive level, for example, a value which can be judged by JCS (Japan Coma Scale) and a daily life independence level. In this example embodiment, a method of judging the level of consciousness and the cognitive level is not limited to the JCS and the daily life independence level, and the level of consciousness and the cognitive level of the patient may be judged by means of other methods.

In this example embodiment, description is made assuming that the acquisition unit 120 acquires the patient information from the outside. However, this is intended as an exemplification and does not limit the present invention. For instance, in the data management system 100, the storage unit 110 may hold the patient information as an electronic medical chart. In this event, the acquisition unit 120 acquires the identifier for identifying the patient from the outside. Then, the acquisition unit 120 may acquire the patient information corresponding to the identifier from the storage unit 110.

FIG. 3 is a view for illustrating one example of the patient information 300 acquired by the acquisition unit 120 or the patient information 300 held in the storage unit 110 as the electronic medical chart.

As shown in FIG. 3, the patient information 300 includes, for each patient, an identifier for identifying the patient, an age, sex, a state of the patient, an examination item, and so on. Specifically, as an example of the patient information 300, it is shown, for example, that a patient having a patient ID of "0001" and a patient name of "AAAA" is a "male" having the age of "24", that a score of the MMT as a state of the patient is "4", and that the examination items to be executed are an "examination A" and an "examination C". The patient information 300 herein includes the patient ID and the patient name as the identifier but may include either one. In addition, although the score of the MMT is shown as the state of the patient in this example embodiment, a score judged by means of other methods may be used. Although the examination items include three kinds of examinations: the examination A, an examination B, and the examination C, this is intended as an exemplification and does not limit the present invention. The number of the examinations included in the patient information 300 is not limited.

Based on the examination information 200 illustrated in FIG. 2 and the patient information 300 illustrated in FIG. 3, the calculation unit 130 calculates, in accordance with the patients, a travel time required for traveling from an examination or consultation location at which an examination or consultation already completed has been performed to a next examination or consultation location at which a next examination or consultation subsequent the examination or consultation is to be performed. In addition, when the acquisition unit 120 acquires the patient information relating to a plurality of patients, the calculation unit 130 can calculate, for each of the plurality of patients, the travel time required for traveling from the examination or consultation location to the next examination or consultation location.

The calculation unit 130 can calculate a distance between respective examinations based on the examination information 200 because the examination information 200 includes the examination locations at which the respective examinations are performed. Specifically, for example, the storage unit 110 holds map information of a medical institution and the calculation unit 130 can calculate the distance between the examinations based on the map information. In addition, the calculation unit 130 can calculate the travel time between the respective examinations based on the distance between the examinations. In this event, in order to calculate the travel time between the examinations in the calculation unit 130, for example, the storage unit 110 may hold information relating to an average travel speed which corresponds to the state of the patient, such as paralysis.

FIG. 4 is a view for illustrating one example of speed information 400 representing correspondences between the states of the patients and the travel speeds held in the storage unit 110.

As shown in FIG. 4, the speed information 400 includes information relating to the travel speed for each state of the patient. Specifically, in the speed information 400, for example, it is shown that the travel speed of the patient having a score of "0" is "V0". In this event, the calculation unit 130 can calculate the time required for the patient to travel between the examinations by dividing the calculated distance between the examinations by the travel speed included in the speed information 400.

In addition, the storage unit 110 may hold, instead of the speed information, correspondence information, for example, representing correspondences between the states of the patients and the travel times required for traveling between the respective examinations.

FIG. 5 is a view for illustrating the correspondence information 500 representing the correspondences between the paralysis states of the patients and the travel times. As shown in FIG. 5, the correspondence information 500 represents the correspondences between the states of the patients and the travel times required for traveling between the respective examinations. Specifically, in the correspondence information 500, a patient having a score of "0" requires a travel time T1 between the examination A and the examination B, a travel time T2 between the examination A and the examination C, and a travel time T3 between the examination B and the examination C. The correspondence information 500 may be common to those patients with the same score as the state of the patient or correspondence information specific to each patient may be used.

In such a case, first, the acquisition unit 120 acquires, for example, the patient information of the patient name of "AAAA" in the patient information 300 illustrated in FIG. 3 and the correspondence information 500. As a result, the calculation unit 130 can calculate the required time for traveling between the examination A and the examination C as "T14" minutes based on the correspondence information 500 because the state of the patient of "AAAA" is "4" and the examinations to undergo are the "examination A" and the "examination C".

In addition, the calculation unit 130 may calculate not only the travel time between the examinations but also a time required for the patient to make preparation in order to undergo the examination, such as a time required for changing clothes in order to perform the examination. In this event, the storage unit 110 may hold information of associating the state of the patient with the time required for the patient to make preparation in order to undergo the examination. As a result, the calculation unit 130 can calculates the time required for the patient to make preparation in order to undergo the examination in a manner similar to that of the method of calculating the travel time between the examinations.

The generating unit 140 generates an examination schedule for the patient based on the examination information, the patient information, and the travel time. Although the examination schedule will be described later, the generating unit 140 can generate the examination schedule with the travel time between the examinations used as a margin between the respective examinations. Specifically, in a case where the patient having the patient name of "AAAA" performs the "examination C" after the "examination A", the generating unit 140 generates the examination schedule by adding, to the required examination time of 20 minutes for the examination C illustrated in FIG. 2, "T14" minutes as the margin. Herein, the margin between the examinations means, for example, the travel time required for traveling from the examination location to the next examination location and the time required for changing clothes in order to perform the examination in the next examination location. In addition, the generating unit 140 may set, as the margin between the examinations, the time required for the patient to make preparation in order to undergo the examination. Furthermore, the generating unit 140 may set a margin having a different width in accordance with the examination. As a result, the generating unit 140 can generate the examination schedule with the examination and the travel time between the examinations associated with each other.

In addition, when the acquisition unit 120 acquires the patient information relating to a plurality of patients, the generating unit 140 can generate examination schedules with appropriate margins between the examinations set for each of the plurality of patients. Furthermore, the generating unit 140 can generate the examination schedule so that, for the examination required to widen the margin between the examinations, the examination can be preferentially performed at an early time. This is because, when the examination required to widen the margin between the examinations is scheduled in a plurality of time zones, there is a possibility that a lot of waiting times occur in each time zone. As a result, the generating unit 140 can further reduce the waiting times for undergoing the examinations by generating the examination schedule so that the examination required to widen the margin between the examinations is preferentially performed for the patient.

When the acquisition unit 120 acquires, after generating the examination schedule, the patient information of an emergency patient required to urgently perform the examinations, the generating unit 140 renews the examination schedule so that the emergency patient can preferentially undergo the examinations. In this event, the generating unit 140 can automatically renew the examination schedule, for example, when the acquisition unit 120 acquires the patient information of the emergency patient. In addition, when the acquisition unit 120 acquires the patient information of the emergency patient required to urgently perform the examinations, the generating unit 140 may cancel the examination schedule already generated. In this event, the generating unit 140 newly generates an examination schedule such that the emergency patient can preferentially undergo the examinations.

It is noted that an example of renewing the examination schedule by the generating unit 140 is not limited to a case where the emergency patient appears. The generating unit 140 may renew the examination schedule when a difference between a reservation and an actual result exceeds a predetermined threshold, for example, due to a reason such as a trouble in an examination apparatus.

Figure 6A:
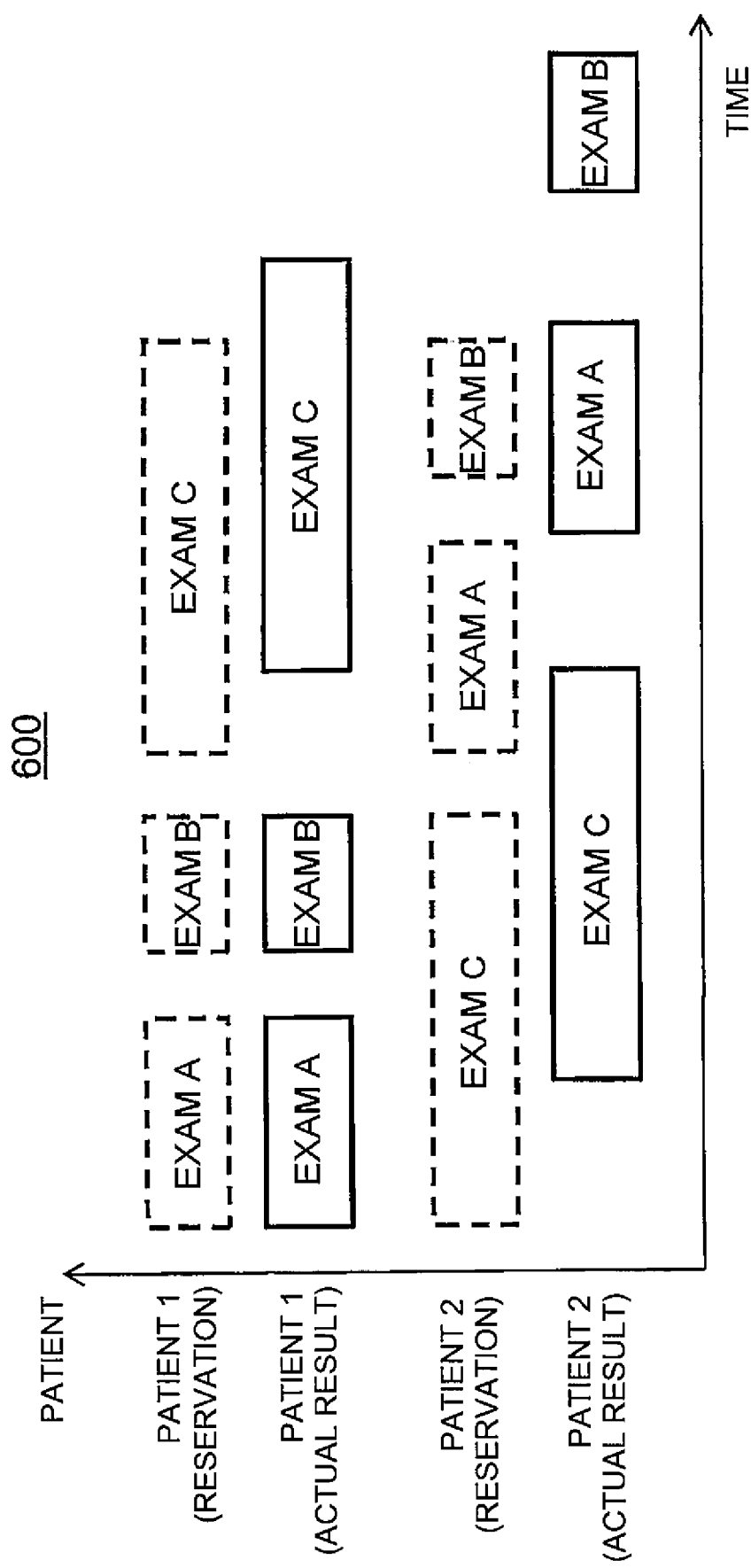
FIG. 6A is a view for illustrating one example of an examination schedule generated by a data management system according to a related art of the present invention.
Figure 6B:
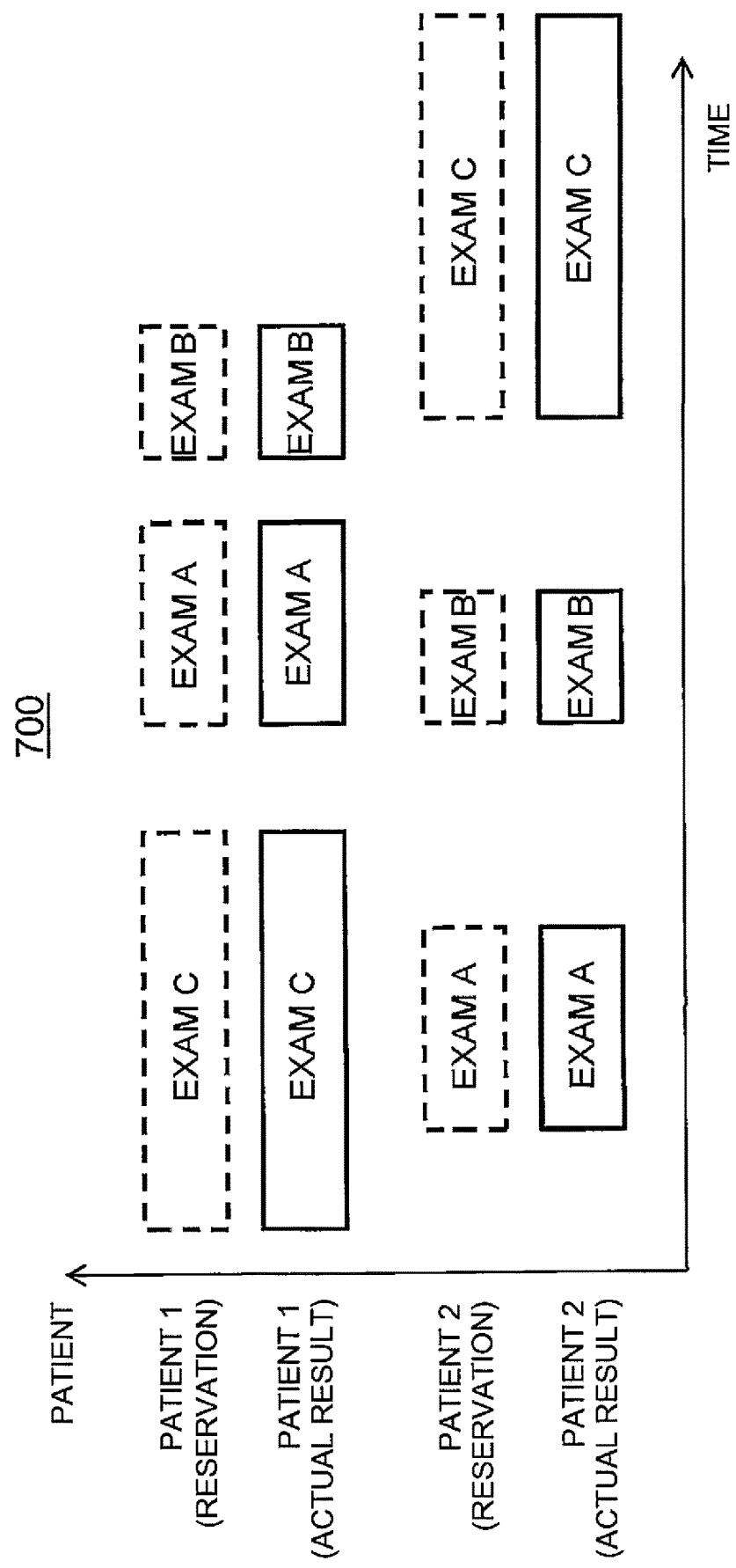
FIG. 6B is a view for illustrating one example of an examination schedule generated by the data management system according to the first example embodiment of the present invention.

Now, description will proceed to the examination schedule generated by the data management system 100. FIG. 6A is a view for illustrating one example of an examination schedule 600 generated by a data management system according to the related art, which is disclosed in Patent Literature 1. FIG. 6B is a view for illustrating one example of an examination schedule 700 generated by the data management system 100 according to this example embodiment. Herein, it is assumed that a patient 1 and a patient 2 undergo a series of an examination A, an examination B, and an examination C in different orders from each other.

The examination schedule 600 illustrated in FIG. 6A and the examination schedule 700 illustrated in FIG. 6B are examination schedules where the ordinate represents information relating to the patients and the abscissa represents a time required for the examinations. In each of the examination schedule 600 and the examination schedule 700, reservation statuses (reservations) for the examinations of the patient 1 and the patient 2 are depicted by broken lines and times (actual results) actually required for the examinations are depicted by solid lines. Specifically, each of the examination schedule 600 and the examination schedule 700 includes, for each of the patient 1 and the patient 2, the reservations and the actual results about three kinds of examinations: the examination A, the examination B, and the examination C.

In the examination schedule 600 and the examination schedule 700, the examination A, the examination B, and the examination C are not specifically limited and may be for example, MM (Magnetic Resonance Imaging), CT (Computed Tomography), electroencephalography, and a blood test. Although each of the examination schedule 600 and the examination schedule 700 includes, as examination items, the three kinds of examinations: the examination A, the examination B, and the examination C, this is intended as an exemplification and does not limit the present invention. The number of examinations included in each of the examination schedule 600 and the examination schedule 700 is not limited.

In addition, in each of the examination schedule 600 and the examination schedule 700, both of the patient 1 and the patient 2 may be patients who visit for the examinations on an outpatient basis or may be patients who are staying in the medical institution. Alternatively, the patient 1 may be an outpatient and the patient 2 may be a patient who is staying in the medical institution. Further, the patients included in the examination schedule 600 and the examination schedule 700 may be a mixture of the patient who visits for the examinations on the outpatient basis and the patient who is staying in the medical institution.

First, in order to facilitate an understanding of the examination schedule generated by the data management system 100 according to the first example embodiment of the present invention, the examination schedule 600 generated by the data management system of the related art of the present invention will be described with reference to FIG. 6A.

In the examination schedule 600, referring to the reservation of the patient 1 and the reservation of the patient 2, scheduling is carried out so that, between the patient 1 and the patient 2, the same examinations do not overlap in the same time zone. In addition, in the examination schedule 600, the margin between the respective examinations is the same for the patient 1 and the patient 2 because the time required for traveling to the examination location and the consultation location is not set in accordance with the patient.

However, referring to the reservation and the actual result for the patient 2, there is a difference between a time of the reservation and a time of the actual result. Specifically, referring to the examination C for the patient 2, a time when the examination C is performed on the patient 2 is late as compared with the reservation time. This is because more times than expected are necessary for the patient 2 to travel to the examination locations for the respective examinations, for example, due to a condition such as paralysis. As a result, an actual examination time when the examination C is performed on the patient 2 overlaps with the reservation time for the patient 1, and a waiting time occurs for the patient 1.

Thus, the times required for traveling from an examination location to a next examination location are different depending on the patients. Therefore, in a case of the data management system of the related art, there is a possibility that a difference between the reservation time and the actual examination time becomes larger as the number of the patients and the number of the examinations are increased. In this event, when the examinations are performed on the patients in accordance with the examination schedule 600, there is a possibility that the patients are required to wait for a long time in order to undergo the examinations, the patients cannot undergo the examinations, and the number of the patients on whom the medical institution can perform the examinations during one day is reduced.

Next, FIG. 6B will be referred to. In the examination schedule 700 generated by the data management system 100 according to the first example embodiment of the present invention, the reservations of the examination A, the examination B, and the examination C for each of the patient 1 and the patient 2 agree with the actual results thereof. This is because the data management system 100 generates the examination schedule 700 after the times required for traveling from an examination or consultation location to a next examination or consultation location are set in accordance with the patients, taking into account an influence of paralysis of the patients or the like.

Specifically, as shown in FIG. 6B, the data management system 100 sets a wider margin between the examinations for the patient 2 as compared with a margin between the examinations for the patient 1 because the travel times between the examinations are taken into account. As a result, according to the examination schedule 700, the patient 1 and the patient 2 can undergo the examinations as scheduled without occurrence of the waiting times for the examinations. In addition, for the medical institution also, it is possible to effectively perform the examinations for a greater number of patients. That is, the data management system 100 can generate the examination schedule which can effectively utilize examination resources by taking the travel time between the examinations into account in accordance with the state of the patient. Such an examination schedule can exhibit a desired effect for both of the patients and the medical institution.

In a case where it is necessary for the patient to change clothes in the respective examinations or the like, the data management system 100 may generate the examination schedule 700 with the time required for changing clothes included in the respective examination times. Furthermore, the data management system 100 may generate the examination schedule 700 with the time required for changing clothes included in the margin between the examinations.

As described above, the data management system 100 can preliminarily generate the examination schedule which can optimally utilize the examination resources of the medical institution. As a result, the medical institution can perform the examinations for a greater number of patients during one day. Such a data management system 100 is especially effective, for example, in a case of generating an examination schedule such as for mass examination in which a plurality of examinations are performed on a large number of patients during one day.

[Operation of Data Management System 100]

Figure 7:
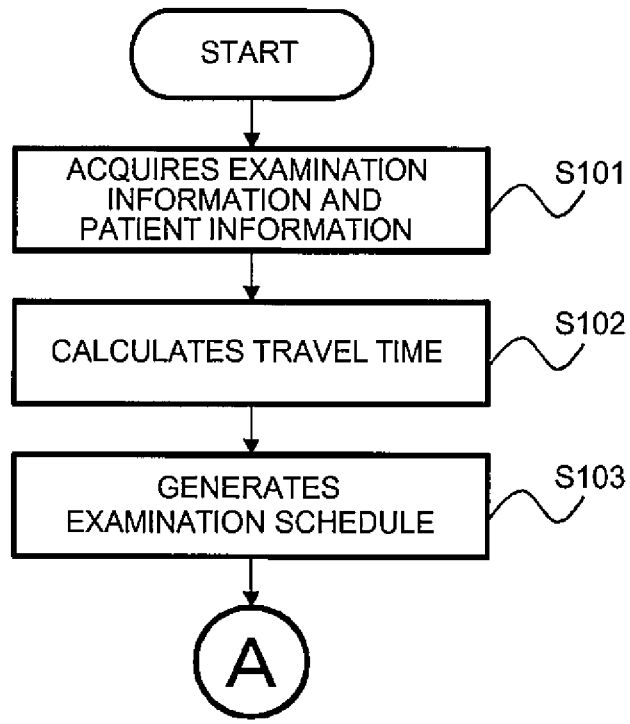
FIG. 7 is a flow chart for illustrating a flow of operation of the data management system according to the first example embodiment of the present invention.

FIG. 7 is a flow chart for illustrating a flow of operation of the data management system 100. Referring now to FIGS. 1 and 7, description will proceed to the flow of operation of the data management system 100.

First, the acquisition unit 120 acquires, from the outside, the patient information of the patient to be examined and acquires, from the storage unit 110, the examination information corresponding to the patient information (step S101).

Subsequently, the calculation unit 130 calculates, based on the examination information and the patient information, the travel time required for traveling from an examination or consultation location to a next examination or consultation location (step S102).

Subsequently, the generating unit 140 generates, based on the examination information, the patient information, and the travel time, the examination schedule with the examinations associated with the travel times between the examinations (step S103).

Now, description will proceed to a flow of operation for the data management system 100 to renew the examination schedule when an emergency patient appears.

Figure 8:
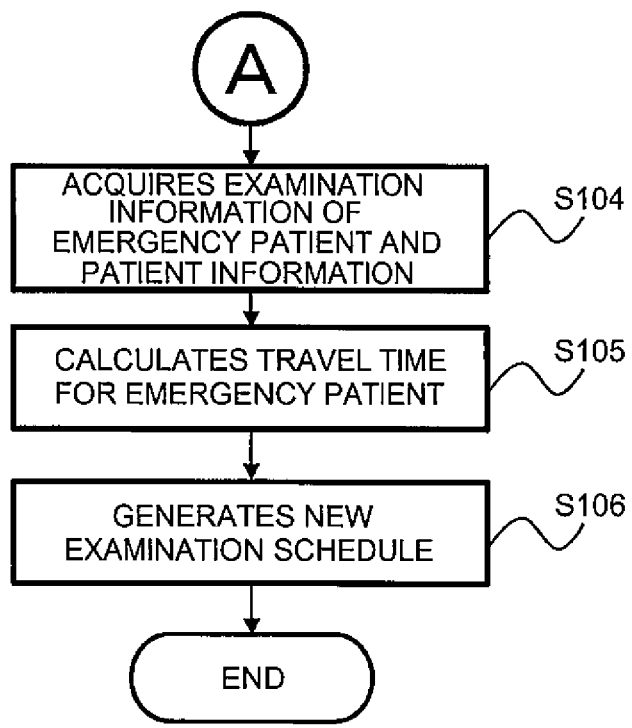
FIG. 8 is a flow chart for illustrating a flow of operation of generating a new examination schedule by the data management system according to the first example embodiment of the present invention.

FIG. 8 is a flow chart for illustrating a flow of operation for the data management system 100 to cancel the present examination schedule and to generate a new examination schedule in a case of receiving the patient information of the emergency patient.

When the emergency patient appears after generating the examination schedule in the step S103 illustrated in FIG. 7, the acquisition unit 120 acquires the patient information of the emergency patient and acquires, from the storage unit 110, the examination information corresponding to the patient information (step S104).

Subsequently, the calculation unit 130 calculates, based on the examination information and the patient information of the emergency patient, the travel time required for traveling from an examination or consultation location to a next examination or consultation location (step S105).

Subsequently, the generating unit 140 renews, based on the information acquired in the step S104 and the travel time calculated in the step S105, the examination schedule so that the emergency patient preferentially undergoes the examinations (step S106).

The data management system 100 is configured to automatically perform the above-mentioned steps S104 to S106 in a case of acquiring the patient information of the emergency patient. With the above-mentioned configuration, in a case where the emergency patient appears and the examination schedule must be rearranged, the data management system 100 can quickly renew the examination schedule so that the emergency patient can preferentially undergo the examinations.

Second Example Embodiment

Figure 9:
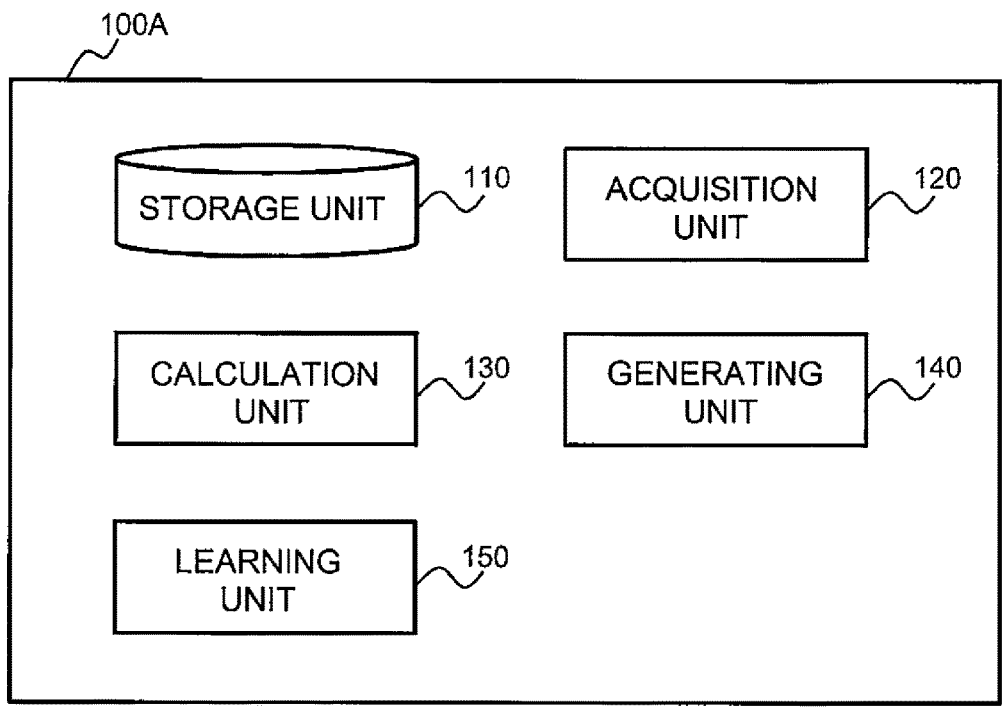
FIG. 9 is a block diagram for illustrating a data management system according to a second example embodiment of the present invention.

FIG. 9 is a block diagram for illustrating a configuration of a data management system 100A according to a second example embodiment of the present invention.

As shown in FIG. 9, the data management system 100A comprises the storage unit 110, the acquisition unit 120, the calculation unit 130, the generating unit 140, and a learning unit 150.

The learning unit 150 is configured to learn, by means of machine learning, a correlation between the examination information and the patient information. The learning unit 150 calculates a model expression representing a correspondence, for example, between the paralysis state of the patient and the travel time required for traveling from an examination or consultation location to a next examination or consultation location, and repeatedly learns the model expression for a plurality of patients. As a result, the learning unit 150 can learn the correlation between the paralysis state of the patient and the travel time. In addition, the learning unit 150 may learn a correlation between the travel time and a motor function, an age, a level of consciousness, and a cognitive level of the patient without being limited to the paralysis state of the patient.

The learning unit 150 comprises a storage area (not shown) for storing a result having been learned as a learned result. Herein, the learning unit 150 may store the learned result in the storage unit 110 in place of the storage area itself. In the data management system 100A, the generating unit 140 generates the examination schedule based on the examination information, the patient information, and the learned result of the learning unit 150.

[Operation of Data Management System 100A]

Figure 10:
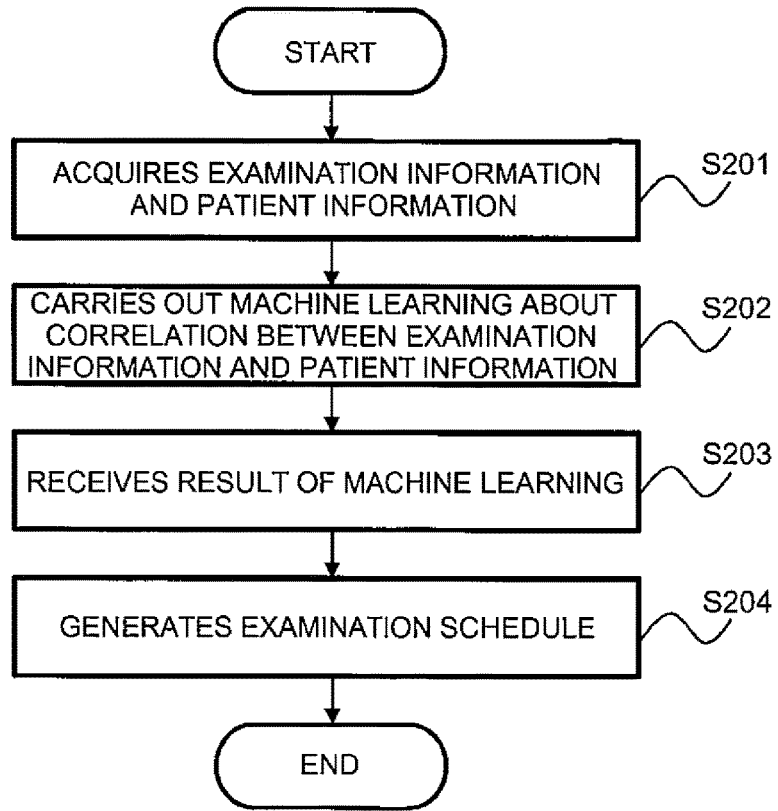
FIG. 10 is a flow chart for illustrating a flow of operation of the data management system according to the second example embodiment of the present invention.

FIG. 10 is a flow chart for illustrating a flow of operation until the data management system 100A generates the examination schedule based on the leaned result of the machine learning. Referring now to FIG. 10, description will proceed to the flow of operation of the data management system 100A.

First, the learning unit 150 receives the patient information from the outside and acquires the examination information from the storage unit 110 (step S201). Subsequently, the learning unit 150 learns, by means of machine learning, the correlation between the patient information and the examination information (step S202).

The generating unit 140 receives the learned result from the learning unit 150 (step S203). Then, the generating unit 140 generates the examination schedule using the learned result (step S204).

As described above, the data management system 100A learns, by means of machine learning, the correlation between the patient information and the examination information. As a result, the data management system 100A can generate, for each patient, the examination schedule in which the travel time required for traveling from the examination or consultation location to the next examination or consultation location is more accurately reflected.

[Hardware Configuration of the Data Management System]

The above-mentioned data management system 100 and the data management system 100A may be implemented by hardware or may be implemented by software. In addition, the data management system 100 and the data management system 100A may be implemented by a combination of hardware and software.

Figure 11:
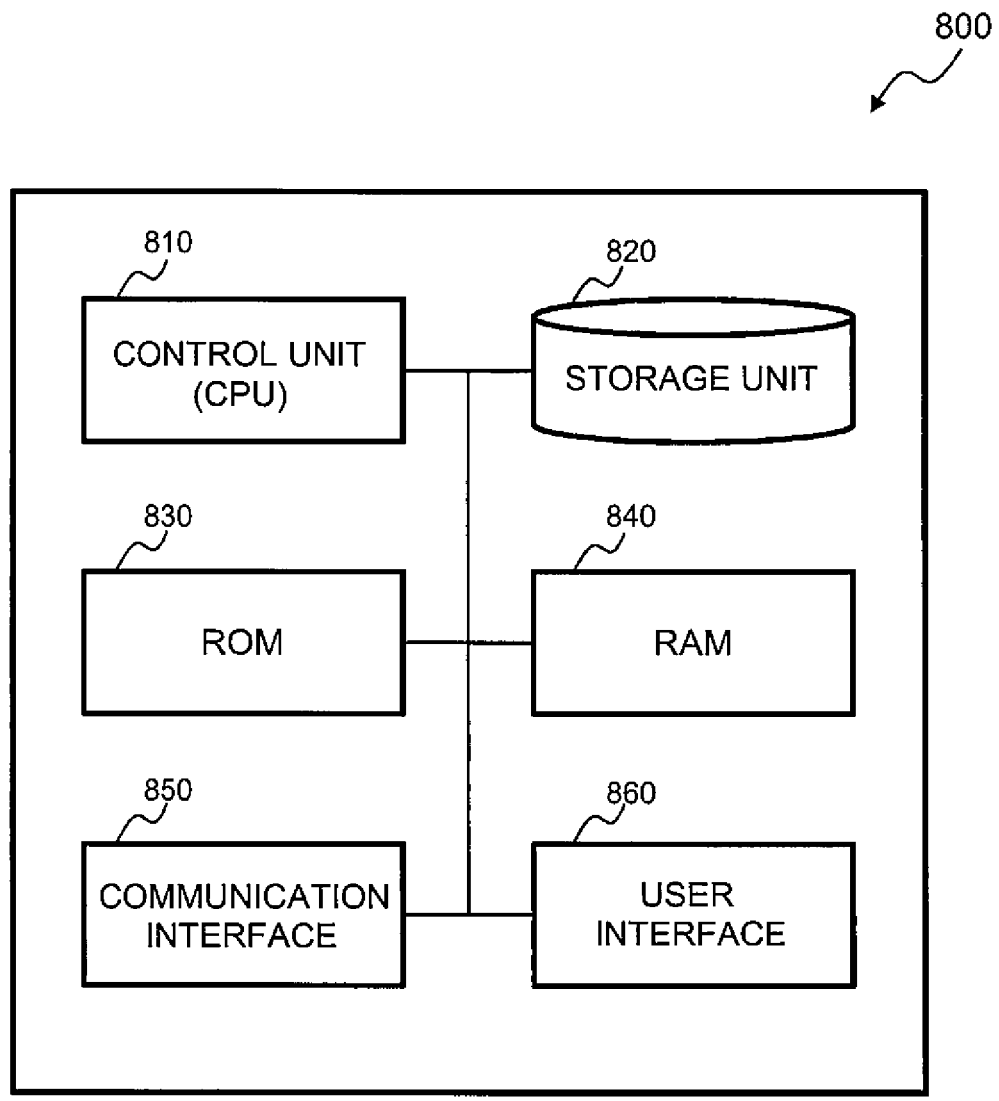
FIG. 11 is a block diagram for illustrating an example of hardware configuration of the data management systems according to the first and the second example embodiments of the present invention.

FIG. 11 is a block diagram for illustrating one example of an information processing apparatus (computer) constituting the data management system 100 and the data management system 100A.

As shown in FIG. 11, the information processing apparatus 800 comprises a control unit (CPU: Central Processing Unit) 810, a storage unit 820, an ROM (Read Only Memory) 830, an RAM (Random Access Memory) 840, a communication interface 850, and a user interface 860.

The control unit (CPU) 810 may implement various functions of the data management system 100 and the data management system 100A by developing, in the RAM 840, a program which is stored in the storage unit 820 or the ROM 830, and by executing the program. In addition, the control unit (CPU) 810 may comprise an internal buffer which is adapted to temporarily store data or the like.

The storage unit 820 comprises a bulk storage medium which can hold various types of data and may be implemented by a storage medium such as an HDD (Hard Disk Drive) and an SSD (Solid State Drive). The storage unit 820 may be a cloud storage existing in a communication network when the information processing apparatus 800 is connected to the communication network via the communication interface 850. The storage unit 820 may hold the program readable by the control unit (CPU) 810.

The ROM 830 is a nonvolatile storage device which may comprise a flash memory having a small capacity as compared to the storage unit 820. The ROM 830 may hold a program which is readable by the control unit (CPU) 810. The program readable by the control unit (CPU) 810 may be held in at least one of the storage unit 820 and the ROM 830.

The program readable by the control unit (CPU) 810 may be supplied to the information processing apparatus 800 in a state where it is non-transitorily stored in various storage media readable by the computer. Such storage media include, for example, a magnetic tape, a magnetic disk, a magneto-optical disc, a CD-ROM (Compact Disc-Read Only Memory), a CD-R (Compact Disc-Readable), a CD-RW (Compact Disc-ReWritable), and a semiconductor memory.

The RAM 840 comprises a semiconductor memory such as a DRAM (Dynamic Random Access Memory) and an SRAM (Static Random Access Memory) and may be used as an internal buffer which temporarily stores data and so on.

The communication interface 850 is an interface which connects the information processing system 800 and the communication network via wire or wirelessly.

The user interface 860 comprises, for example, a display unit such as a display and an input unit such as a key board, a mouse, and a touch panel.

While the present invention has been shown and described with reference to example embodiments thereof, the present invention is not limited to the foregoing embodiments. It will be understood by those skilled in the art that various changes in form and details of the present invention by be made without departing from the spirit and scope of the present invention.

A part or a whole of the example embodiments described above may also be described as the following supplementary notes without being limited thereto.

(Supplementary Note 1)

A data management system, comprising a storage unit configured to store examination information including at least examination items which include examination names of a plurality of examinations, examination locations at which the examinations are performed, consultation locations at which consultations are performed, and required examination times which are required for the respective examinations; an acquisition unit configured to acquire patient information relating to an identifier for identifying a patient to be examined and degree of severity thereof; a calculation unit configured to calculate, in accordance with the patient, a travel time required for traveling from an examination or consultation location at which an examination or consultation already completed has been performed to a next examination or consultation location at which a next examination or consultation subsequent to the examination or consultation is to be performed, based on the patient information and the examination information; and a generating unit configured to generate an examination schedule for the patient based on the examination information, the patient information, and the travel time.

(Supplementary Note 2)

The data management system according to Supplementary Note 1, further comprising a learning unit configured to machine-learn a correlation between the examination information and the patient information, wherein the generating unit is configured to generate the examination schedule using a learned result of the learning unit.

(Supplementary Note 3)

The data management system according to Supplementary Note 1 or 2, wherein, when the acquisition unit acquires the patient information relating to a plurality of patients, the calculating unit calculates, for each of the plurality of patients, the travel time required for traveling from the examination or consultation location to the next examination or consultation location, and the generating unit generates the examination schedule for each of the plurality of patients based on the examination information, the patient information, and the travel time for each of the plurality of patients.

(Supplementary Note 4)

The data management system according to any one of Supplementary Notes 1 to 3, wherein the generating unit is configured to provide a priority order for the examinations of the examination names included in the examination items in accordance with a degree of influence exerted by a state of the patient upon the required examination time and to generate the examination schedule with the priority order taken into account.

(Supplementary Note 5)

The data management system according to any one of Supplementary Notes 1 to 4, wherein, when the acquisition unit receives information indicative of appearance of an emergency patient, the generating unit automatically renews the examination schedule so that the emergency patient preferentially undergoes the examinations.

(Supplementary Note 6)

The data management system according to any one of Supplementary Notes 1 to 5, wherein the patient information includes at least one of a paralysis state, an age, a level of consciousness, a cognitive level, a motor function of the patient.

(Supplementary Note 7)

A data management method, performed by an information processing apparatus, comprising storing examination information including at least examination items which include examination names of a plurality of examinations, examination locations at which the examinations are performed, consultation locations at which consultations are performed, and required examination times which are required for the respective examinations; acquiring patient information relating to an identifier for identifying a patient to be examined and degree of severity thereof; calculating, in accordance with the patient, a travel time required for traveling from an examination or consultation location at which an examination or consultation already completed has been performed to a next examination or consultation location at which a next examination or consultation subsequent to the examination or consultation is to be performed, based on the patient information and the examination information; and generating an examination schedule for the patient based on the examination information, the patient information, and the travel time.

(Supplementary Note 8)

The data management method according to Supplementary Note 7, performed by the information processing apparatus, comprising machine-learning a correlation between the examination information and the patient information; and generating the examination schedule using a learned result of the machine learning.

(Supplementary Note 9)

The data management method according to Supplementary Note 7 or 8, performed by the information processing apparatus, comprising, when the patient information relating to a plurality of patients are acquired calculating the travel time required for traveling from the examination or consultation location to the next examination or consultation location for each of the plurality of patients, and generating the examination schedule for each of the plurality of patients based on the examination information, the patient information, and the travel times for each of the plurality of patients.

(Supplementary Note 10)

The data management method according to any one of Supplementary Notes 7 to 9, wherein, by the information processing apparatus, a priority order for the examinations of the examination names included in the examination items is provided in accordance with a degree of influence exerted by a state of the patient upon the required examination time and the examination schedule is generated with the priority order taken into account.

(Supplementary Note 11)

The data management method according to any one of Supplementary Notes 7 to 10, wherein, when information indicative of appearance of an emergency patient is received by the acquisition unit, the examination schedule is automatically renewed by the information processing apparatus so that the emergency patient preferentially undergoes the examinations.

(Supplementary Note 12)

The data management method according to any one of Supplementary Notes 7 to 11, wherein the patient information includes at least one of a paralysis state, an age, a level of consciousness, a cognitive level, a motor function of the patient.

(Supplementary Note 13)

A recording medium for storing a data management program which causes a computer to execute the procedures of storing examination information including at least examination items which include examination names of a plurality of examinations, examination locations at which the examinations are performed, consultation locations at which consultations are performed, and required examination times which are required for the respective examinations; acquiring patient information relating to an identifier for identifying a patient to be examined and degree of severity thereof; calculating, in accordance with the patient, a travel time required for traveling from an examination or consultation location at which an examination or consultation already completed has been performed to a next examination or consultation location at which a next examination or consultation subsequent to the examination or consultation is to be performed, based on the patient information and the examination information; and generating an examination schedule for the patient based on the examination information, the patient information, and the travel time.

(Supplementary Note 14)

The data management program recording medium according to Supplementary Note 13, wherein the data management program causes the computer to execute the procedures of machine-learning a correlation between the examination information and the patient information; and generating the examination schedule using a learned result of the machine learning.

(Supplementary Note 15)

The data management program recording medium according to Supplementary Note 13 or 14, wherein the data management program causes the computer to execute, when the patient information relating to a plurality of patients are acquired, the procedures of calculating, for each of the plurality of patients, the travel time required for traveling from the examination or consultation location to the next examination or consultation location, and generating the examination schedule for each of the plurality of patients based on the examination information, the patient information, and the travel time for each of the plurality of patients.

(Supplementary Note 16)

The data management program recording medium according to any one of Supplementary Notes 13 to 15, wherein the data management program causes the computer to execute the procedure of providing a priority order for the examinations of the examination names included in the examination items in accordance with a degree of influence exerted by a state of the patient upon the required examination time and generating the examination schedule with the priority order taken into account.

(Supplementary Note 17)

The data management program recording medium according to any one of Supplementary Notes 13 to 16, wherein the data management program causes the computer to execute, when information indicative of appearance of an emergency patient is received, the procedure of automatically renewing the examination schedule so that the emergency patient preferentially undergoes the examinations.

(Supplementary Note 18)

The data management program recording medium according to any one of Supplementary Notes 13 to 17, wherein the patient information includes at least one of a paralysis state, an age, a level of consciousness, a cognitive level, a motor function of the patient.

REFERENCE SIGNS LIST 100, 100A data management system
110 storage unit
120 acquisition unit
130 calculation unit
140 generating unit
150 learning unit
200 examination information
300 patient information
400 speed information
500 correspondence information
600, 700 examination schedule
800 information processing apparatus
810 control unit (CPU)
820 storage unit
830 ROM
840 RAM
850 communication interface
860 user interface

The invention claimed is:

1. A data management system for preparing an examination schedule to perform a plurality of examinations for a patient, the data management system comprising:
a storage unit configured to store examination information including at least examination items which include examination names of a plurality of examinations, examination locations at which the examinations are performed, and required examination times which are required for the respective examinations;
an acquisition unit configured to acquire patient information relating to an identifier for identifying a patient to be examined and degree of severity thereof;
a calculation unit configured to calculate, in accordance with the patient, a travel time required for the patient to travel from an examination location at which an examination already completed has been performed to a next examination location at which a next examination subsequent to the examination is to be performed, based on the patient information and the examination information; and
a generating unit configured to generate the examination schedule for the patient based on the examination information, the patient information, and the travel time.

2. The data management system as claimed in claim 1, further comprising a learning unit configured to machine-learn a correlation between the examination information and the patient information,
wherein the generating unit is configured to generate the examination schedule using a learned result of the learning unit.

3. The data management system as claimed in claim 1, wherein, when the acquisition unit acquires the patient information relating to a plurality of patients,
the calculating unit calculates, for each of the plurality of patients, the travel time required for traveling from the examination location to the next examination location, and
the generating unit generates the examination schedule for each of the plurality of patients based on the examination information, the patient information, and the travel time for each of the plurality of patients.

4. The data management system as claimed in claim 1, wherein the generating unit is configured to provide a priority order for the examinations of the examination names included in the examination items in accordance with a degree of influence exerted by a state of the patient upon the required examination time and to generate the examination schedule with the priority order taken into account.

5. The data management system as claimed in claim 1, wherein, when the acquisition unit receives information indicative of appearance of an emergency patient, the generating unit automatically renews the examination schedule so that the emergency patient preferentially undergoes the examinations.

6. The data management system as claimed in claim 1, wherein the patient information includes at least one of a paralysis state, an age, a level of consciousness, a cognitive level, a motor function of the patient.

7. The data management system as claimed in claim 1, wherein the patient information includes at least a motor function of the patient,
wherein the motor function includes a value which is judged by at least one of a MMT (Manual Muscle Test), a FIM (Functional Independence Measure), and a BI (Barthel Index).

8. A data management method for preparing an examination schedule to perform a plurality of examinations for a patient, the data management method comprising:
storing examination information including at least examination items which include examination names of a plurality of examinations, examination locations at which the examinations are performed, and required examination times which are required for the respective examinations;
acquiring patient information relating to an identifier for identifying a patient to be examined and degree of severity thereof;
calculating, in accordance with the patient, a travel time required for the patient to travel from an examination location at which an examination already completed has been performed to a next examination location at which a next examination subsequent to the examination is to be performed, based on the patient information and the examination information; and
generating the examination schedule for the patient based on the examination information, the patient information, and the travel time.

9. The data management method as claimed in claim 8, comprising:
machine-learning a correlation between the examination information and the patient information; and
generating the examination schedule using a learned result of the machine learning.

10. The data management method as claimed in claim 8 comprising, when the patient information relating to a plurality of patients are acquired:
calculating the travel time required for traveling from the examination location to the next examination location for each of the plurality of patients, and generating the examination schedule for each of the plurality of patients based on the examination information, the patient information, and the travel times for each of the plurality of patients.

11. The data management method as claimed in claim 8, wherein, a priority order for the examinations of the examination names included in the examination items is provided in accordance with a degree of influence exerted by a state of the patient upon the required examination time and the examination schedule is generated with the priority order taken into account.

12. The data management method as claimed in claim 8, wherein, when information indicative of appearance of an emergency patient is received the examination schedule is automatically renewed so that the emergency patient preferentially undergoes the examinations.

13. The data management method as claimed in claim 8, wherein the patient information includes at least one of a paralysis state, an age, a level of consciousness, a cognitive level, a motor function of the patient.

14. A non-transitory computer readable recording medium recording a data management program for preparing an examination schedule to perform a plurality of examinations for a patient which causes a computer to execute the procedures of:
   storing examination information including at least examination items which include examination names of a plurality of examinations, examination locations at which the examinations are performed, and required examination times which are required for the respective examinations;
   acquiring patient information relating to an identifier for identifying a patient to be examined and degree of severity thereof;
   calculating, in accordance with the patient, a travel time required for the patient to travel from an examination location at which an examination already completed has been performed to a next examination location at which a next examination subsequent to the examination is to be performed, based on the patient information and the examination information; and
   generating the examination schedule for the patient based on the examination information, the patient information, and the travel time.

15. The non-transitory computer readable recording medium as claimed in claim 14, wherein the data management program causes the computer to execute the procedures of:
   machine-learning a correlation between the examination information and the patient information; and
   generating the examination schedule using a learned result of the machine learning.

16. The non-transitory computer readable recording medium as claimed in claim 14, wherein the data management program causes the computer to execute, when the patient information relating to a plurality of patients are acquired, the procedures of:
   calculating, for each of the plurality of patients, the travel time required for traveling from the examination location to the next examination location, and
   generating the examination schedule for each of the plurality of patients based on the examination information, the patient information, and the travel time for each of the plurality of patients.

17. The non-transitory computer readable recording medium as claimed in claim 14, wherein the data management program causes the computer to execute the procedure of:
   providing a priority order for the examinations of the examination names included in the examination items in accordance with a degree of influence exerted by a state of the patient upon the required examination time and generating the examination schedule with the priority order taken into account.

18. The non-transitory computer readable recording medium as claimed in claim 14, wherein the data management program causes the computer to execute, when information indicative of appearance of an emergency patient is received, the procedure of:
   automatically renewing the examination schedule so that the emergency patient preferentially undergoes the examinations.

19. The non-transitory computer readable recording medium as claimed in claim 14, wherein the patient information includes at least one of a paralysis state, an age, a level of consciousness, a cognitive level, a motor function of the patient.

* * * * *